(12) United States Patent
Bouchalat

(10) Patent No.: US 6,171,499 B1
(45) Date of Patent: Jan. 9, 2001

(54) OPTIMISED METHOD FOR THE TREATMENT AND ENERGETIC UPGRADING OF URBAN AND INDUSTRIAL SLUDGE PURIFYING PLANTS

(76) Inventor: Youssef Bouchalat, 15A, rue de Geaune, F-68128 Village-Neuf (FR)

(*) Notice: Under 35 U.S.C. 154(b), the term of this patent shall be extended for 0 days.

(21) Appl. No.: 09/142,195

(22) PCT Filed: Oct. 13, 1997

(86) PCT No.: PCT/FR97/01819

§ 371 Date: Sep. 2, 1998

§ 102(e) Date: Sep. 2, 1998

(87) PCT Pub. No.: WO98/30506

PCT Pub. Date: Jul. 16, 1998

(30) Foreign Application Priority Data

Jan. 6, 1997 (FR) .................................................. 97 00050

(51) Int. Cl.$^7$ ...................................................... C02F 3/00
(52) U.S. Cl. ...................... 210/603; 210/605; 210/609; 210/620; 210/630; 210/767; 210/175; 210/919; 210/920
(58) Field of Search .................................. 210/603, 605, 210/609, 620, 630, 767, 175, 919, 920

(56) References Cited

U.S. PATENT DOCUMENTS

| | | | |
|---|---|---|---|
| 3,552,333 | * 1/1971 | Salamon | 110/8 |
| 3,702,596 | * 11/1972 | Winther | 110/8 R |
| 3,954,069 | * 5/1976 | Loken | 110/8 R |
| 4,753,181 | * 6/1988 | Sosnowski | 110/346 |
| 5,186,111 | * 2/1993 | Baria | 110/238 |
| 5,360,546 | * 11/1994 | Tomita | 210/603 |
| 5,410,973 | * 5/1995 | Kunstler | 110/246 |
| 5,630,366 | * 5/1997 | Lesoille | 110/221 |

* cited by examiner

Primary Examiner—Chester T. Barry

(57) ABSTRACT

The invention concerns an optimized method for the treatment and energetic upgrading of urban and industrial sewage sludge. It consists of a <<novel>> combination of known and tested equipment, forming a compact assembly with six functions which are: anaerobic sludge digestion (1) and biogas production, mechanical dehydration (2) up to 22–24% of dry solid, a gas turbine installation (3) burning the biogas into <<total energy>>, thermal drying (4) of the sludge up to 92% of dry solid consisting of a thin-layer dryer and a vibrated dryer/cooler with fluid bed (4*b*), condensation of the vapors (5) for heating the digester and the premises, and optimized energetic upgrading (6) of the dried sludge as booster fuel capable of being stored and fed into the household refuse incinerating boiler-furnaces.

The method according to the invention is also applicable to the treatment and transformation of liquid manure into granulated and bagged fertilizer.

10 Claims, 5 Drawing Sheets

(Cf. Fig. 2)

OPTIMISED METHOD FOR THE TREATMENT AND ENERGETIC UPGRADING OF URBAN AND INDUSTRIAL SLUDGE PURIFYING PLANTS

The present invention relates to a method for the treatment and the energetic upgrading of urban and industrial sludge issued from the sewage treatment plants.

The method subject of the claim 1 is characterised by a <<novel>> combination of known and separately tested equipment, allowing to <<liberate>> the energy contained in the sewage sludge and to obtain an energetic positive balance, equal to ≅5.7 tons equivalent petrol/year/1000 equivalent inhabitants.

The method subject of the claim 1 resolves completely the problem of the sewage sludge elimination without pollution transfer, protecting the soil, the ground water and the environment against the bacterial and olfative pollution and against that of the heavy metals; it is characterised that:

1) Its investment cost is competitive and amounts to about 10% of that, for the same equivalent inhabitants number, of a household refuse incineration plant fitted with heat recovery and regulation conformed exhaust gas cleaning.

2) Its automatism is high-efficient with all the securities and allows its automatic running without any human presence, on the understanding that it doesn't use any under pressure steam.

3) Its maintenance is simple and non-expensive; the maintenance staff could come either from the on site sewage treatment plant or from an external maintenance company.

4) Its total cost for the complete sludge treatment per ton is quite competitive in comparison with the cost of a regulation conformed sludge elimination.

It follows an economic incitement to make new investments related to the process subject of the invention, which are therefore profitable and creating a great number of fixed employment by the equipment suppliers.

Today, the problem caused by the sewage sludge makes the local authorities and the State anxious, because of its big and increasing volume, and the risks of its toxic, bacterial and olfative pollution toward the soil, the ground water and the environment. It is therefore urgent to dispose of an optimised method of treatment and valorisation of this sludge which is reliable, durable, non-polluting, cheap and applicable to all cases; that is what the <<process subject of the invention>> proposes, for all the sewage treatment plants with a capacity of 30,000 and more equivalent inhabitants.

The current sewage sludge destination is, after its mechanical dehydration, either the agricultural land spreading or the refuse disposal area, and sometimes its joint incineration with the household refuse, including or not a preliminary thermal drying. This latter destination is expensive and non-optimised regarding to the energetic upgrading of the sludge.

The sewage sludge land disposal is going to disappear due to the dumping prohibition in the European Countries announced for 2002.

The sewage sludge agricultural land spreading, currently more and more widespread, is concerned by the high sludge content of $P_2O_5$ and the relatively low plants need of phosphoric fertiliser which makes the phosphorus as a restricting component and considers the sludge as a <<late>> fertiliser releasing slowly the fertilising elements.

There is a risk of diseases conveying to the man and the animal by the sewage sludge land spreading or land disposal; for example in Switzerland the disease risk is limited because the spread sludge on the agricultural land must be always <<sterile>> and not contain more than 100 germs (enterobacteria) per gram and any contagious worm-egg. Such an obligation doesn't exist in France.

Even after hygienisation, the use of the sludge as a phosphoric late fertiliser must be carried out with <<parsimony>> because of its brought heavy metals, to avoid at a very long-term (see the following table) a soil saturation with heavy metals; in fact the time limit in years to reach the soil saturation with the heavy metals brought by the sludge land spreading of 2.5 t DS/ha/a, in accordance with the Swiss regulation for soil protection, amounts as indicated in the <<EAWAG-News Nr.28 of September 1989>>, for two heavy metals sludge contents, as follows:

| Metal | Medium content mg/kg DS | Time limit in years | Low content mg/kg DS | Time limit in years |
|---|---|---|---|---|
| Zinc | 1500 | 150 | 100 | 240 |
| Copper | 800 | 80 | 250 | 240 |
| Cadmium | 5 | 180 | 1 | 900 |
| Mercury | 5 | 160 | 1 | 800 |

The proceeding of soil <<filling>> till the regulation limit values are reached due to the progressive generalising of the sewage sludge agricultural land spreading, is not in accordance with a good management of the humanity natural patrimony; one has to be careful because the decontamination of polluted soil would be a tedious and much expensive task for the future generations. Besides the prohibition of the sewage sludge land disposal at short-time (2002), is in this consideration very reassuring.

Concerning the organic toxic elements also contained in the sewage sludge that are: LAS (linear alkylbenzéne sulfonate), NP (nonylphénol), PAH (polycyclic aromatic hydrocarbon), Sn-OC (pewter organic combinations), PCB (polychlorobiphényles), HCB (héxachlorobenzene) et LI (lindane), it fails a better risk evaluation of the sewage sludge agricultural use according to the <<EAWAG-News Nr. 28 of September 1989>>.

The method subject of the present invention, allows to stop these inconveniences; it includes the <<energetic upgrading>> of the sludge preliminary dried till 92% DS (dry solid), as a <<booster fuel>> easily storable and to feed it automatically into the household refuse incinerating furnaces, fitted with heat recovery and exhaust gas cleaning installation in order to separate the heavy metals, which will be treated according to the regulation and to the protection of the soil and the ground water.

The dried sludge quantity amounts on average, in France, to <<4.5%>> of the household refuse for the same number of equivalent inhabitants. Its use as a booster fuel will allow to fill the <<hollows>> of the boiler-furnaces thermal load due to the variability of the household refuse humidity and composition, hence of its LHV (low heat value), and to warrant a <<constant>> steam production and equal in so far as possible, to the nominal capacity of the incinerators, thanks to the dried sludge appropriate storage and automatic feeding equipment which is a part of the process subject of the invention, and will be installed on the site of the nearest household refuse incineration plant.

The enclosed diagrams illustrate the <<method>> subject of the invention:

Figure 1:
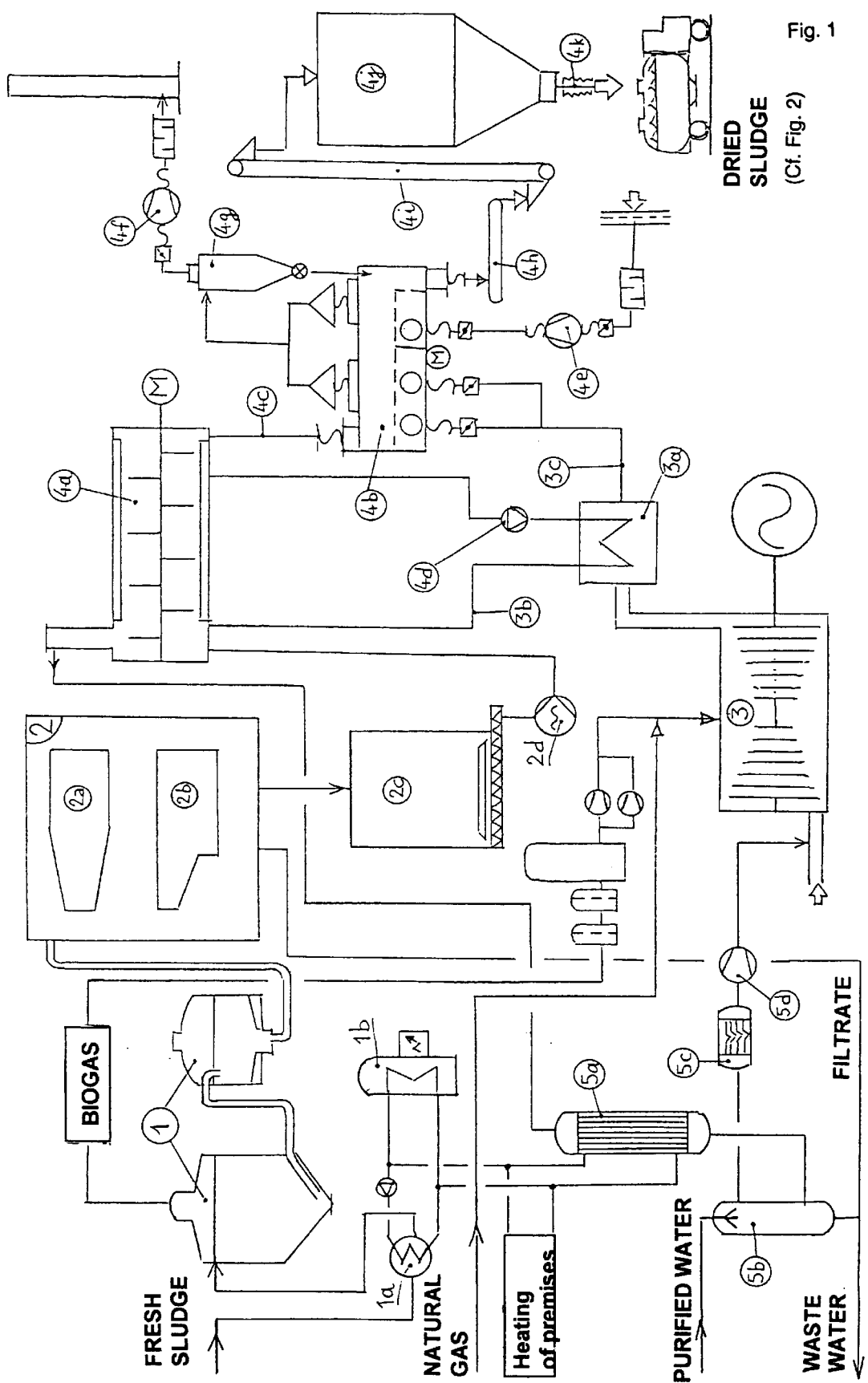
FIG. 1 shows the equipment related to the first five process functions.
Figure 2:
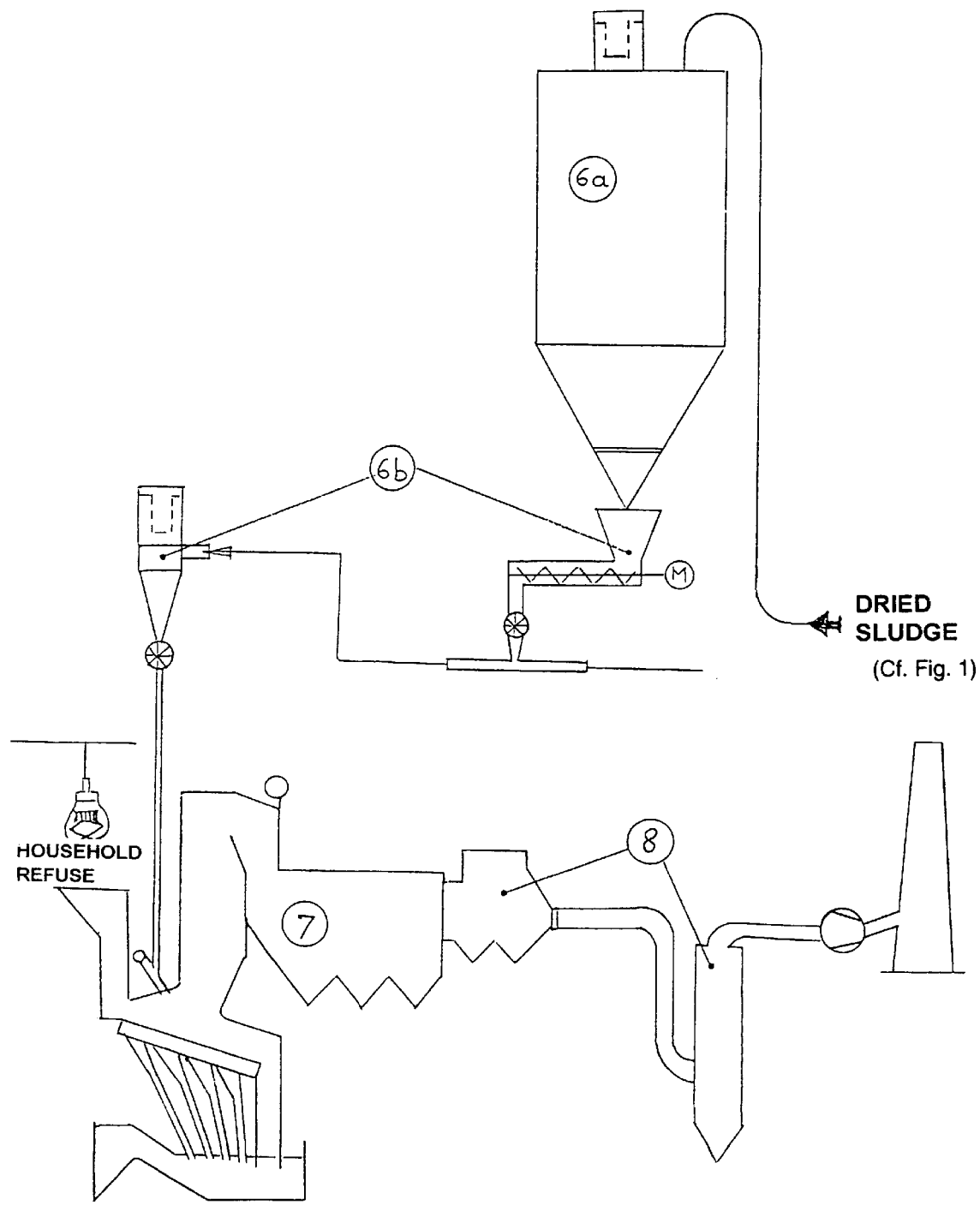
FIG. 2 shows the sixth process function.
Figure 3:
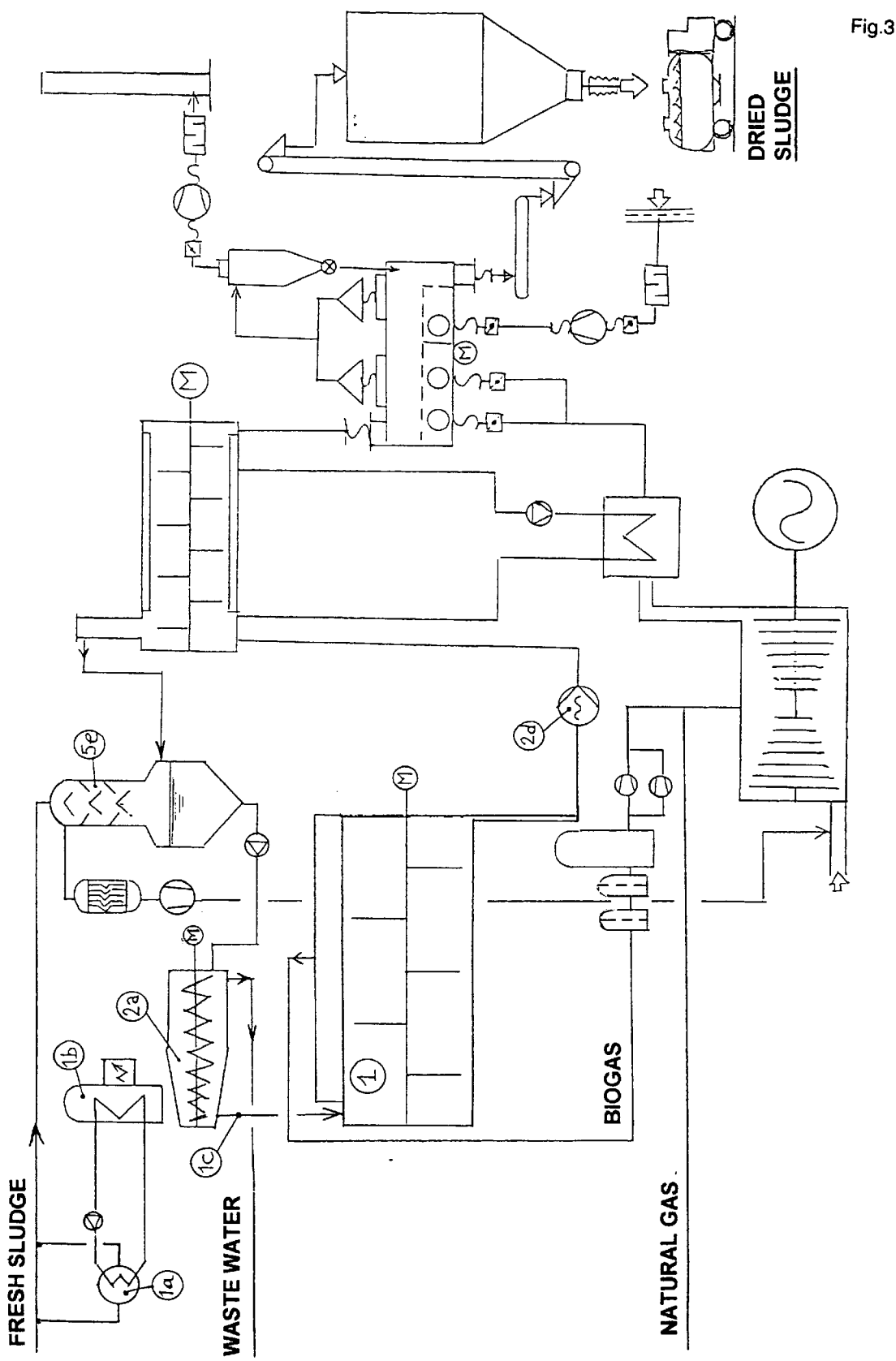
FIG. 3 shows an execution <<variant>> of the process functions 1 and 2.
Figure 4:
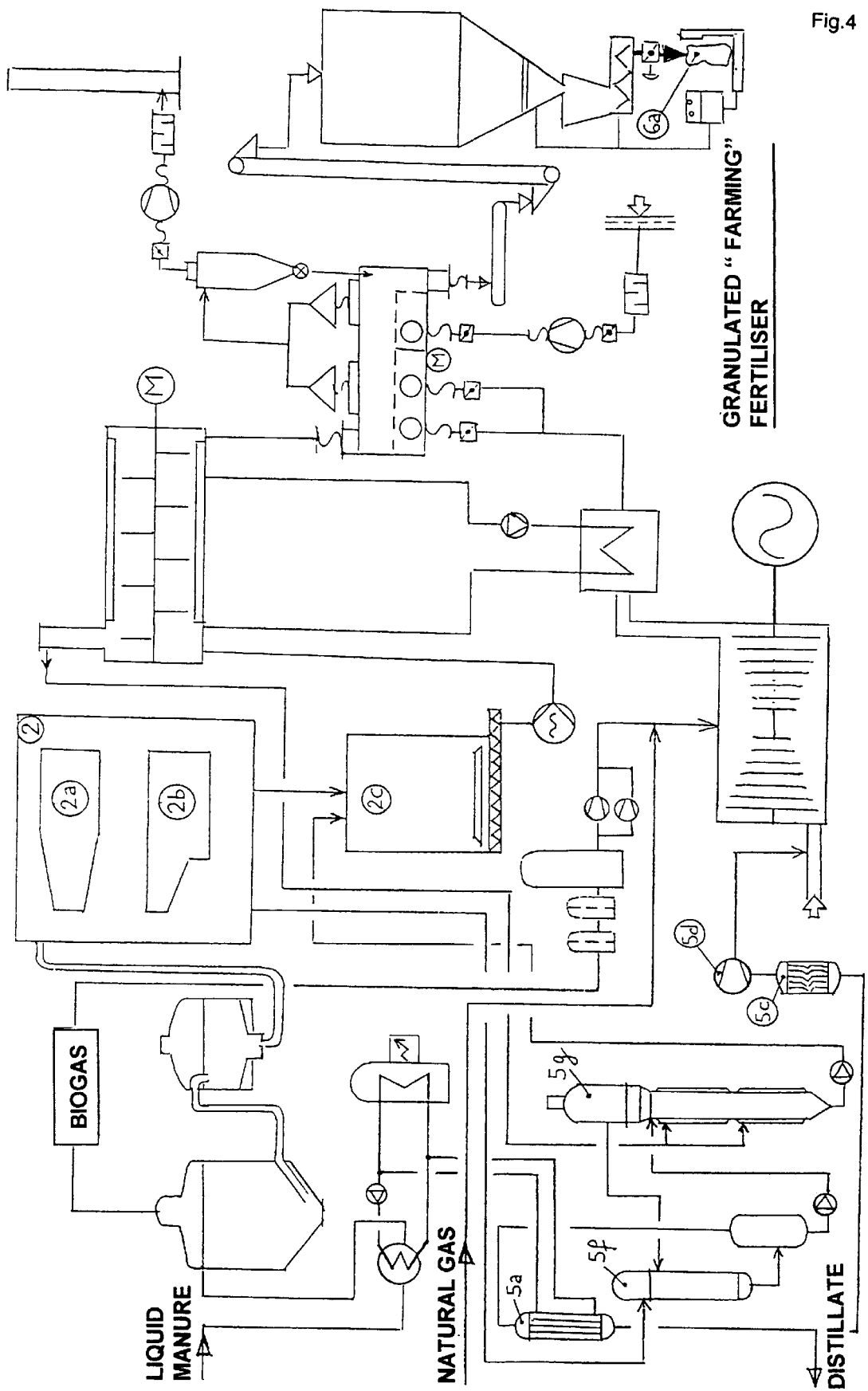
FIGS. 4 and 5 show the process application to the complete treatment of liquid manure and its transformation into a granular fertiliser.
Figure 5:
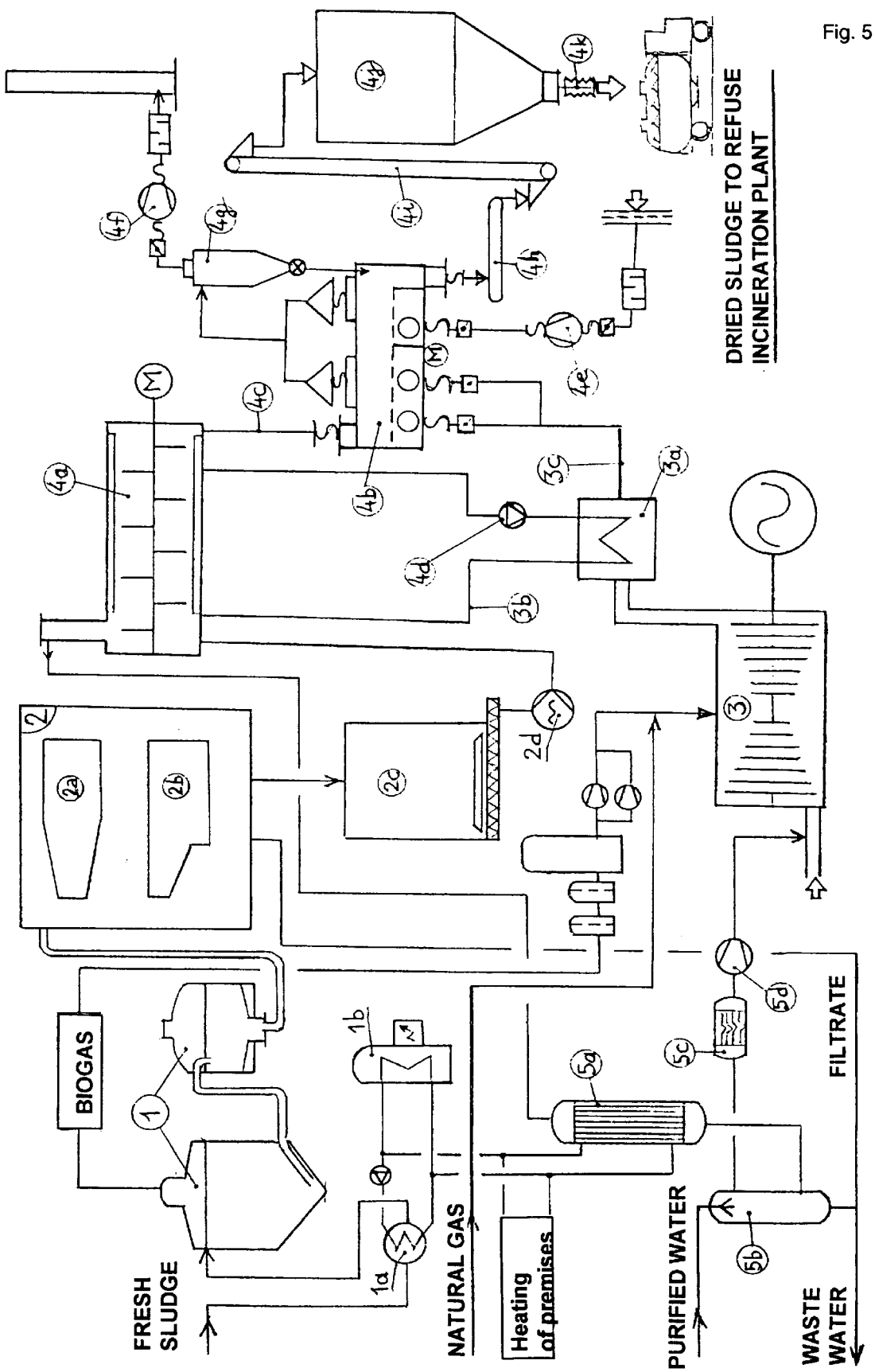

With reference to the diagrams 1 and 2 showing the process flow chart, the description of the functions 1 to 5 for the first time grouped together on the site of a sewage treatment plant, and the function 6 for the first time installed on the site of an incineration plant, is as follows:

1) The anaerobic digestion (1) of liquid fresh sludge which <<liberates>> a part of the sludge energy as biogas, which is treated by dehydration and filtration and stored for its utilisation. The biogas LHV amounts to about 5500 Kcal/Nm$^3$ or 6.395 Kwh/Nm$^3$. In the process according to the invention, the anaerobic digestion is carried out at the temperature of 35° C., airtight during about 20 days in a single conventional reactor. The heating of the liquid fresh sludge is carried out by means of the heat exchanger (1a) using the hot water produced thanks to the condensation heat of the drying vapours. For the first start of the anaerobic digestion a boiler (1b) will assure the heating energy of the sludge by means of the heat exchanger (1a).

According to special execution modes, the conventional anaerobic digestion can be replaced in the process according to the invention, by an anaerobic digestion which separates the two stages of acidogenic hydrolysis and methanogenic fermentation, or by an aerobic thermophilic stabilisation followed by an anaerobic digestion.

2) The mechanical dehydration (2) of the digested sludge till 22 to 24% DS by means of a centrifuge (2a), a filter band press (2b) or any other mechanical dehydration device without any limitation of the final DS content. The sludge mechanical dehydration needs generally the adding of a polymer for the preliminary digested liquid sludge flocculation, allowing the obtaining of an optimal DS content of the dehydrated sludge and a very good quality of the liquid which returns to the sewage treatment plant. The dehydrated sludge is conveyed to the buffer storage silo (2c), then pumped to the thermal drying by means of a special pump (2d). The role of the buffer silo is to run the thermal drying <<continuously>> while the mechanical dehydration can work discontinuously.

3) The combustion of the generated biogas enriched with a light additional natural gas, in a <<gas turbine (3)>> the application of which, subject of the claim 2, is characterised that the heat-power-coupling system runs <<in total energy>>, leading to an increasing of its total output 16% higher than the output of a conventional unit, thanks to its <<judicious>> combination with a sludge thermal drying system comprising two apparatuses, the first of which uses (circuit 3b) the <<100%>> of the recovered energy from the hot gas through the recovery boiler (3a), and the second uses as heating medium (circuit 3c) the <<100%>> of the exhaust gas flow rate out of the boiler (3a) at the outlet temperature, directly without any special adjustment or additional equipment.

According to special execution modes, the gas turbine can be replaced in the process according to the invention, by a gas motor or any other heat-power-coupling system, and the employed fuel can be replaced in the process according to the invention, by only the biogas or only the natural gas.

4) The thermal drying (4) of the mechanical dehydrated sludge till 92% DS and also the cooling of the dried sludge, by means of a system comprising two apparatuses in series, directly joined together by a shaft-fall (4c), <<without>> any upstream wet sludge mixing with recycled dried sludge, and <<without>> any mixing and granulation device between the apparatuses; leading therefore to a great simplification of the sludge <<drying and cooling>> unit.

The description of these two efficient apparatuses, which are included in the process according to the invention, for the sludge drying and then cooling, is as follows:

The first apparatus (4a) is an indirect <<thin-layer rotating dryer>> with a double-mantel heated through a circulating thermal oil, thanks to the circulating pump (4d) through the above mentioned recovery boiler (3a).

According to special execution modes, the recovery boiler (3a) can produce in the process according to the invention, saturated steam under pressure which can be used as heat medium into the double-mantel of the thin-layer dryer instead of the thermal oil.

The heat exchange is carried out through the internal mantel over which the sludge is laid in a thin layer. The heat exchange effect is high because of the weak thickness of the sludge layer, the contact of which with the mantel is intensely renewed thanks to the great thin-layer turbulence produced by a linear speed at the blades extremities of about 8 m/s.

The thin-layer dryer is a well-proved dryer which allows a variability of the dry solid content of the entering sludge, doesn't need a dried sludge recycling and produces dried sludge at the desirable final DS content without any fear of the extremely viscous and sticky phase, so called plastic phase, that the sewage sludge crosses during the drying beyond about 50% DS (dry solid), this limit depends on the sludge type.

The rotor of the thin-layer dryer is fitted with individually adjustable and replaceable blades, which are the cause of the dryer great flexibility and assure the laying of the sludge in a thin layer and its continuous advancing toward the dryer outlet at about 64% DS, i.e. widely beyond the sludge plastic phase, in a granular form thanks to the dryer internal granulation device.

During the drying, the incoming sludge is firstly warmed close to 100° C., then the water contained in the sludge is evaporated at this temperature; due to the sludge warming temperature of 100° C. during the drying, the dried sludge will be sterile and its bacterial pollution will be quasi fully eliminated.

The sludge water evaporation will be pursued in the second drying apparatus (see hereafter) till a dry solid content of about 92% DS obtaining stable and dust free granules; due to the dried sludge final humidity, widely below than 15% water content, any renewal fermentation risk of the dried sludge with bad odours is eliminated.

According to special execution modes, the thin-layer dryer can be replaced in the process according to the invention, by any other dryer type.

The second apparatus (4b) is a vibrated dryer/cooler with fluid bed which carries out the final sludge drying from 64% DS to about 92% DS by means of the exhaust hot gas out of the recovery boiler (3a) through a fixed perforated plate.

The pre-dried sludge at about 64% DS and at the temperature of about 100° C., falls directly per gravity into the shaft-fall (4c) of the vibrated dryer (4b); in fact the internal granulation device of the thin-layer dryer and the dry solid content of the pre-dried sludge, beyond the sludge plastic phase, give to the pre-dried sludge an optimal structure for the final drying by a vibrated fluid bed dryer, without any mixing and granulating of the pre-dried sludge with recycled dried sludge, between the two apparatuses.

The same vibrated dryer (4b) includes at the end of the drying zone a separated zone through which fresh air blows by means of ventilators (4e) and (4f) allowing the cooling of the dried sludge at 92% DS till a temperature lower than 50° C., compatible with its ulterior storage.

The vibrated dryer/cooler (4b) doesn't comprise any rotating blades which grind the sludge producing fine dust of dried sludge; therefore the sludge granules formerly produced by the thin-layer dryer are not broken by the vibrated dryer/cooler, only their size is slightly reduced due to the reduction of their humidity. It follows that no dust is contained in the final dried product and in the exhaust gas; however a cyclone separator (4g) is put, as a security measure, in the exhaust gas circuit.

The cooled dried sludge is fed by a band conveyer (4h) fitted with a translucent cover, and a bucket elevator (4i) into a storage silo (4j) fitted with a loading set (4k), then it will be transported by a lorry fitted with a pneumatic unloading system to the nearest household refuse incineration plant.

According to special execution modes, the vibrated fluid bed dryer can be replaced in the process according to the invention, by any other dryer type, likewise the security cyclone separator can be either deleted or replaced by any other device such as a bag filter.

5) The condensation of the vapours (5) coming out of the indirect thin-layer dryer with the condensation heat recovery by means of the tubular exchanger (5a). This energy recovery of the vapours as hot water, is used to warm the liquid fresh sludge for the anaerobic digestion and to heat in winter the sewage treatment plant premises. In case of possible vapours excess, the spray condenser (5b) is used by means of an injection of treatment plant cooling water, and it is designed to condense, in case of need, the totality of the vapours issued from the thin-layer dryer.

The volatile compounds of the sludge, such as: mercaptans, formaldehyde and hydrogen sulphide, are carried away with the vapours out of the indirect thin-layer dryer where the sludge is pre-dried till about 64% DS; at this stage the all volatile malodorous compounds are evaporated and carried away with the vapours to the condensers, after which the uncondensable gases amounting to a low flow rate are conveyed through a demister (5c) by means of a fan (5d) to the burner of the gas turbine, in order to be incinerated and so thermally deodorised; therefore the pre-dried sludge at 64% DS is rid of the volatile malodorous compounds and can be dried by the vibrated dryer with fluid bed by means of the hot exhaust gas without any risk of a great olfactive pollution transfer, so that the deodorisation of the exhaust gas after the vibrated dryer/cooler is not necessary, leading therefore to a great simplification of the process according to the invention.

According to special execution modes, in the process according to the invention, the deodorisation of the uncondensable gases out of the condensers can be carried out either by a chemical or biological way, and the vibrated drier/cooler can be fitted, in the process according to the invention, with an exhaust gas deodorisation system.

6) The <<optimised>> energetic upgrading of the dried sludge at about 92% DS, subject of the claim 3, is characterised as follows:

The dried sludge representing a low volume, is transported by lorry to the nearest household refuse incineration plant where, within the process subject of the invention, adequate dried sludge storage silo (6a) and automatic feeding system (6b) are installed.

The dried sludge the LHV (low heat value) of which amounts to about 2270 Kcal/Kg or 2.64 Kwh/Kg, is automatically fed into the boiler-furnace (7) on the basis of the desired steam flow rate to be produced, it fills the oscillation hollows of the thermal load related to the household refuse incineration till a horizontal line corresponding to the nominal thermal load of the boiler-furnace, without any overloading of the existing equipment of the household refuse incineration plant. This mode of energetic upgrading of the dried sludge allows the advantage for the household refuse incineration plant, to benefit from a booster fuel easily to be stored and conveyed in order to produce a <<constant>> steam flow rate and to <<warrant>> a constant energy supply to a third party.

A household refuse incineration plant is considered capable to burn the dried sludge, if it is fitted in addition to the heat recovery system, with an exhaust gas cleaning unit (8) according to the current regulations for the protection of the soil, the ground water and the environment, particularly the separation of the heavy metals issued from the household refuse and the dried sludge. In consideration of the relative low proportion of the dried sludge to the household refuse, generally equal to 4.5%, as mentioned page 4 line 21, the elimination of the heavy metals issued from the dried sludge will lead to a <<marginal>> cost which has to be determined and compared, from case to case, with the profit of the energy recovered from the dried sludge.

According to special execution modes, the destination of the dried sludge can be in the process according to the invention, different from that above described one, such as any other incineration plant.

All the equipment of piping, measurements and regulations, handling and storage of the sludge etc . . . , is characterised that it will be chosen at the head of the technique on the date of each carrying out of the process according to the invention; the schematic representations of this equipment figuring on the enclosed process flow chart are not restricted.

The process according to the invention reduces the sewage sludge volume, depending on the sludge treatment steps, as indicated in the following table:

| Sewage sludge in T/1000 E.Inh./a: | | | | |
| --- | --- | --- | --- | --- |
| fresh S. (4–5% DS) | digested S. (4–5% DS) | dehydrated S. (22–24% DS) | dried S. (92% DS) | incinerated S. (100% min.mat.) |
| 511 | 350,5 | 104,5 | 17,14 | 7,82 |

With reference to the diagram 3, the <<variant>> subject of the claim 4, of the process subject of the invention, is characterised that the process functions 3, 4 and 6 are unchanged, and that the functions 1, 2 and 5 can be carried out, as a novel way, within the process as follows: the liquid fresh sludge is heated up to the temperature of 55–60° C. in the mix-condenser (5e) of the vapours issued from the thin-layer dryer, then continuously dehydrated by a centrifuge (2a) with a preliminary adding of polymer, the polymer quantity needed will be lower and the dry solid content of the dehydrated fresh sludge will be higher, due to the temperature increase to 55–60° C. For the first time of the fresh sludge heating, one will use the boiler (1b) and the heat exchanger (1a) which, if necessary, could be used as additional heating device.

The dehydrated sludge at 28–30% DS is directly fed through a shaft-fall (1c), into the horizontal thermophilic anaerobic digester (1), fitted with an agitator to homogenise the sludge during the digestion and for an optimal biogas release; the digester volume is much more little due to the dry solid content increase to 28–30% DS of the entering fresh sludge, instead of 4–5% DS, leading to a digester volume reduction of about 6 times for an unchanged residence time.

The digested sludge is extracted continuously at the end of the horizontal reactor, and is fed by means of a special pump (2d) directly, without any intermediate storage silo, to the digested sludge thermal drying unit.

The horizontal digester includes a sufficient volume reserve to respond to an untimely stop of the sludge thermal drying. The nominal residence time of the sludge in the reactor amounts to about 20 days.

Then the process functions 3, 4 and 6 are carried out as unchanged.

With reference to the diagram 4, the <<application>> subject of the claim 5, of the process subject of the invention, for the liquid <<manure>> treatment, is characterised that the process functions 1, 2, 3 and 4 are unchanged, and that the functions 5 and 6 can be carried out, as a novel way, within the process as follows:

The condensation of the vapours issued from the indirect thin-layer dryer is carried out on the one hand by the tubular condenser (5a) producing the hot water for the anaerobic digester heating, and on the other hand by a thin-film evaporator (5g) fitted with moving rotor blades which touch by running the heated surface, in order to end the concentration at about 20% DS, of the <<liquid>> issued from the mechanical dehydration of the manure; the pre-concentration of this liquid is carried out by means of a multistage evaporation unit (5f) with falling film evaporators; the concentrate at about 20% DS is fed into the buffer storage silo (2c); the distillate, as a cleaned water, is used for irrigation or directly released to the water course. The uncondensable gases out of the condensers amounting to a low flow rate are conveyed through a demister (5c) by means of a fan (5d) to the burner of the gas turbine, in order to be incinerated and so thermally deodorised.

The dried manure is used as a granulated <<farming>> fertiliser, bagged by means of the sacking machine (6a); it is rich in nutriments and will be used as a matter of priority according to the needs of the plants, without any overdosing, with the same regard as to a commercial fertiliser.

What is claimed is:

1. A method for the treatment and the reuse as solid fuel of urban and industrial sewage sludge, characterized in that it comprises the following steps:
    a) the anaerobic sludge digestion (1), in one stage or in two stages, and biogas production;
    b) the mechanical dehydration (2) of the digested sludge;
    c) the biogas combustion, enriched with addition of natural gas, in a gas turbine (3) running with an overall energy yield of about 88%;
    d) the thermal drying of the dehydrated sludge by means of two apparatuses in series: the first apparatus is an indirect thin-layer dryer (4a) with a double-mantle heated by a circulating thermal oil (3b) through the boiler (3a) recovering the heat issued from the biogas combustion, the second apparatus is a vibrated fluid bed dryer and cooler (4b), heated by the exhaust hot gas (3c) out of the recovery heat exchanger and followed by a cyclone separator (4g) in the exhaust gas circuit;
    e) the condensation of the vapors coming out of the indirect thin-layer dryer, with a thermal deodorization of the uncondensable gases in the burner of the gas turbine, by means of a tubular condenser (5a) producing the hot water used to warm the digester and the premises, and a mix-condenser (5b), as stand-by, to condense the excess vapors in summer time by means of a spray of purified water issued from the sewage treatment plant;
    f) transporting the dried sludge to a household refuse incineration plant, and use of the dried sludge as a "booster" fuel which is easily storable in a silo (6a) and automatically conveyed (6b), according to the demand of the existing boiler-furnaces (7), in order to fill or to equalize their thermal load and to utilize the existing capacity of the incineration plant's equipment, including that related to the heavy metals elimination (8).

2. The process according to claim 1, wherein the generated energy through the biogas combustion in a heat-power-coupling unit, corresponding to the $3^{rd}$ step of the process of claim 1, is used for the thermal drying of either the sewage sludge or the manure, due to two adequate dryers: the first one (4a), a thin-layer dryer, is indirectly heated by the thermal oil (3b) produced by the recovery boiler (3a), and the second one, a vibrated fluid bed dryer, is directly heated by the boiler exhaust gas (3c) issued from the biogas combustion.

3. The process according to claim 1, wherein the dried sludge has an approximate lower heating value of about 2270 Kcal/Kg, is used as low-energy fuel by household refuse incineration plants fitted with the heat recovery system and the heavy metals elimination unit.

4. The process according to claim 1, wherein the liquid fresh sludge is firstly mechanically dehydrated, by a continuous centrifuge (2a), then thermophilic anaerobic digestion in a horizontal reactor (1); the fresh sludge heating up to the temperature of 55–60° C. directly uses the latent heat of the vapors issued from the thin-layer dryer (4a), in a mix-condenser (5e) fitted with cascades; this high temperature of the fresh sludge improves the centrifuge performance, giving a dehydrated sludge at 28–30% DS, that is directly fed into the digester at the desired temperature and moves forward due to a "piston effect" till the extremity, then pumped (2d) to the thin-layer dryer (4a); the functions 3, 4 and 6 of the process of claim 1 are then carried out as specified in claim 1.

5. The process according to claim 1 wherein, for the treatment of the livestock manure and its transformation into granulated fertilizer, further comprising the steps of:
    distillation of the liquid issued from the manure mechanical dehydration; which is at first pre-concentrated by means of a multistage evaporation unit (5f) with falling film evaporators, then concentrated till about 20% dry solid by means of a thin-film evaporator (5g) fitted with moving rotor blades, using the supplied energy from the excess vapors compared with the digester heating need; and
    use of the dried manure, after its cooling and storage, as a granulated "farming" fertilizer, which is bagged by means of the sacking machine (6a).

6. The process according to claim 1, wherein the gas turbine (3) is replaced by a gas motor or any other heat-power-coupling system.

7. The process according to claim 1, wherein the indirect thin-layer dryer (4a) or the vibrated fluid bed dryer (4b) are replaced, together or separately, by any other type of dryers.

8. The process according to claim 1, wherein the cyclone separator (4g) is either deleted or replaced by any other device such as a bag filter.

9. The process according to claim 1, wherein the deodorization of the uncondensable gases or the exhaust gas, is carried out either by a chemical or a biological way.

10. The process according to claim 1, wherein the dried sludge is not used as a booster fuel by a refuse incineration plant, but by any other incineration plant.

* * * * *